United States Patent [19]

Amundsen et al.

[11] Patent Number: 4,786,725
[45] Date of Patent: Nov. 22, 1988

[54] SOLUBILIZED PLATINUM (II) COMPLEXES

[75] Inventors: Alan R. Amundsen, Somerville; Eric W. Stern, Mountain side, both of N.J.

[73] Assignee: Engelhard Corporation, Menlo Park, N.J.

[21] Appl. No.: 835,584

[22] Filed: Mar. 3, 1986

Related U.S. Application Data

[60] Continuation of Ser. No. 660,617, Oct. 12, 1984, abandoned, which is a division of Ser. No. 392,818, Jun. 28, 1982, Pat. No. 4,500,465.

[51] Int. Cl.$^4$ .............................................. C07H 23/00
[52] U.S. Cl. ..................................... 536/121; 536/18.7; 549/206; 549/315; 556/137
[58] Field of Search ................ 556/137; 514/492, 91, 514/114, 184; 536/121, 18.7; 549/315, 206

[56] References Cited

U.S. PATENT DOCUMENTS

| 4,410,544 | 6/1983 | Berg et al. | 556/137 X |
| 4,410,707 | 6/1983 | Cleare et al. | 556/137 |
| 4,431,666 | 2/1984 | Bulten et al. | 556/137 X |
| 4,500,465 | 2/1985 | Amundsen et al. | 556/17 |
| 4,587,331 | 5/1986 | Hlavka et al. | 536/22 X |

FOREIGN PATENT DOCUMENTS 2019399 10/1979 United Kingdom .
2128615  5/1984 United Kingdom .

Primary Examiner—H. M. S. Sneed
Assistant Examiner—George R. Fourson

[57] ABSTRACT

There are described platinum-polyhydroxylated amine compounds which exhibit anti-tumor activity in mammalian species. The products are highly soluble in aqueous solutions and they may be administered either orally or in parenteral form.

1 Claim, No Drawings

SOLUBILIZED PLATINUM (II) COMPLEXES

This is a continuation of application Ser. No. 660,617 filed 10/12/84, now abandoned which is a divisional of 392,818 filed 6/28/82 now U.S. Pat. No. 4,500,465.

This invention relates to a novel class of platinum-containing compoounds which contain a polyhydroxylated amine as a solubilizing component.

This invention also relates to pharmaceutical compositions which contain said compounds as an active ingredient and to a method for the treatment of tumors via the administration of said compositions.

The known platinum complexes do not, as a rule, exhibit high solubility in aqueous solutions and this factor limitstheir usefulness as active agents in tumor therapy.

It is an object of this invention to add to the known family of anti-tumor agents by providing a new class of platinum complexes which are highly soluble in water and which combine the advantages of high activity with low mammalian toxicity.

BACKGROUND

The discovery that some platinum complexes are active against tumors has brought about a renewed interest in metal complexes as a source for anti-cancer agents. Cisplatin, cis-[Pt(NH$_3$)$_2$Cl$_2$], for example, has been singularly successful in bringing about a regression of testicular and ovarian tumors and, as a result, other platinum derivatives have been investigated for anti-tumor activity. This led to the extensive testing of platinum and other transition metal compounds for anti-tumor activity in animals (Cleare; "Coordination Chemistry Reviews"; 12: 349 (1974); and Connors and Roberts, ed., "Platinum Coordination Complexes in Cancer Chemotherapy", Springer; New York (1974)). The neutral complexes: cis-[PtA$_2$X$_2$] have been shown to be most active against animal tumors but, as a class, they are not very soluble in water (J. L. Marx; "Science", 192: 774 (1976)). Cleare and Hoeschele indicate solubilities in water or saline which range from 0.04 g/100 ml for [Pt(CH$_3$NH$_2$)$_2$(malonate)] to 1.38 g/100 ml for [Pt(CH$_3$NH$_2$)$_2$Cl$_2$] at 37° (Cleare and Hoeschele, "Bioinorganic Chemistry"; 2: 187 (1973)). Unfortunately, such low solubilities render them less desirable for oral or intravenous administration.

THE INVENTION

It is an object of this invention to provide a novel class of highly soluble platinum compounds which contain polyhydroxylated monodentate or bidentate amines as solubilizing components and which are useful as anti-tumor agents in mammals.

These compounds are highly soluble in water and they may be employed as active ingredients in aqueous fluids for the parenteral or oral treatment of tumors. They exhibit excellent activity against malignant tumors in animals as well as low mammalian toxicity.

Specifically, this invention relates to a platinum-amine compound of the formula: cis-[Pt(A)$_2$(X)$_2$] (I) wherein A represents a polyhydroxylated amine; A$_2$ represents a polyhydroxylated diamine and the X radicals are anionic ligands selected from among halo and carboxylato or, taken together, the X radicals represent dicarboxylato, sulfato, orthophosphato, or pyrophosphato or a combination of aquo and sulfato, orthophosphato, or pyrophosphato.

More precisely, this invention relates to platinum-amine complexes of the following formula:

wherein:

A is a polyhydroxy substituted monodentate amine of the formula:

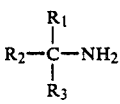

wherein R$_1$, R$_2$, and R$_3$ are selected from the group consisting of hydrogen, C$_{1-6}$ alkyl, or C$_{1-6}$ mono or polyhydroxyalkyl, provided that R$_1$, R$_2$, and R$_3$, taken together, contain two or more hydroxy groups, or A$_2$ is a polyhydroxy substituted bidentate amine of the formula:

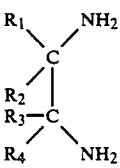

wherein R$_1$, R$_2$, R$_3$, and R$_4$ are selected from the group consisting of H, C$_{1-6}$ alkyl, or C$_{1-6}$ mono or polyhydroxyalkyl provided that R$_1$-R$_4$ taken together contain two or more hydroxyl groups, or wherein R$_2$ and R$_3$, taken together with the carbon atoms to which they are attached, represent C$_{5-7}$ alkylene containing two or more hydroxyl groups, or A$_2$ is a polyhydroxy substituted bidentate amine of the formula:

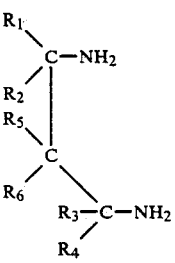

wherein R$_1$, R$_2$, R$_3$, and R$_4$ are selected from the group consisting of hydrogen, C$_{1-6}$ alkyl, or C$_{1-6}$ mono or polyhydroxyalkyl, and R$_5$ and R$_6$ are selected from the group consisting of hydrogen, hydroxy, C$_{1-6}$ alkyl, or C$_{1-6}$ mono or polyhydroxyalkyl provided that R$_1$-R$_6$ taken together contain two or more hydroxyl groups, or A$_2$ is a polyhydroxy substituted bidentate amine of the formula:

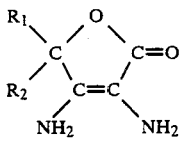

wherein $R_1$ and $R_2$ are selected from the group consisting of hydrogen, $C_{1-6}$ alkyl, or $C_{1-6}$ mono or polyhydroxyalkyl provided that $R_1$ and $R_2$ taken together contain two or more hydroxyl groups, or A is a polyhydroxy substituted monodentate amine of the formula:

$R_1NH_2$ wherein $R_1$ is a carbohydrate moiety derived from glucose, fructose, galactose, sucrose, lactose, and the like; and X is an anionic ligand selected from the group consisting of halide, for example chloride, bromide or iodide, or a carboxylate, for example acetate, propionate, lactate, or bromoacetate, or $X_2$ is a dicarboxylate anion, for example malonate, ethylmalonate, cyclobutanedicarboxylate, succinate, and phthalate, or $X_2$ is sulfate, orthophosphate, or pyrophosphate, or $X_2$ is the combination of aquo and sulfate, orthophosphate, or pyrophosphate.

A preferred embodiment of this invention relates to products of the formula:

wherein A is a polyhydroxy substituted modentate amine of the formula:

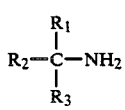

wherein $R_1$, $R_2$, and $R_3$ are selected from the group consisting of hydrogen, $C_{1-6}$ alkyl, or $C_{1-6}$ mono or polyhydroxyalkyl, provided that $R_1$, $R_2$, and $R_3$, taken together, contain two or more hydroxyl groups and X is a halide anion, preferably chloride.

This embodiment or class of products exhibits excellent activity against animal tumors and excellent solubility in aqueous fluids which enhances their usefulness for oral and parenteral administration.

PREPARATIVE METHODS

The products of this invention may be prepared by treating potassium tetrachloroplatinate with a stoichiometric amount of potassium iodide in aqueous solution. The intermediate which forms, potassium tetraiodoplatinate, is then combined with a polyhydroxy amine or diamine (A or $A_2$) to afford cis-$[Pt(A)_2I_2]$ or cis-$[PtA_2I_2]$. This product may be separated from solution or the iodo moieties may be replaced by other anions as, for example, by chloro, bromo, or carboxylate anions via treatment with silver nitrate and the appropriate acid or salt. The following equation illustrates the preparation of cis-$[Pt(A)_2Cl_2]$ from the corresponding iodo precursor but the dibromo analog of this complex may be obtained in a similar manner by simply providing in solution an adequate concentration of the desired anion:

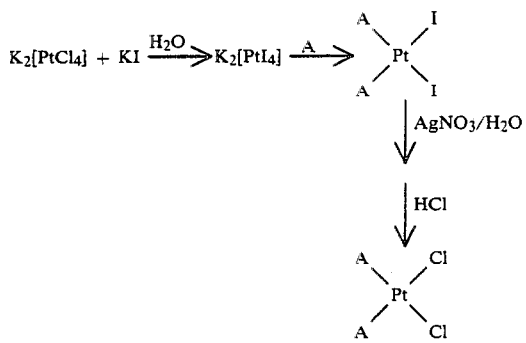

In this process platinum chloride or lithium tetrachloroplatinate may be substituted for $K_2[PtCl_4]$ to afford an identical potassium tetraiodoplatinate intermediate. The reaction with lithium tetrachloroplatinate may be conducted in ethanol instead of water.

Also, it is possible to substitute for silver nitrate any of the following equivalent reagents: silver sulphate ($AgSO_4$), silver perchlorate ($AgClO_4$) or silver fluoborate ($AgBF_4$).

An alternative method for preparing products in which the solubilizing ligand is a diamine consists of first treating $K_2[PtCl_4]$ with an equimolar amount of said diamine to form the Pt(II)-bidentate complex directly. If the complex which forms is so highly soluble that it will not precipitate from solution then the reaction medium may be evaporated to a low volume under vacuum, whereupon, the potassium chloride in solution can be precipitated by the careful addition of ethanol. The Pt(II) bidentate complex which remains in solution can then be isolated by conventional techniques.

PHARMACOLOGY

The products of this invention are useful in the treatment of malignant animal tumor cells in animals as for example sarcoma 180 ascites in mammals such as mice. This anti-tumor cell effect may also extend to other sarcomas and to such other tumor cells as the following: lymphoid leukemia, lymphosarcoma, myelocytic leukemia, malignant lymphoma, squamos cell carcinoma, adenocarcinoma, scirrhous carcinoma, malignant melanoma, seminoma, teratoma, choriocarcinoma, embryonalcarcinoma, cystadenocarcinoma, endometroidcarcinoma or neuroblastoma and the like. In addition, said complexes may be useful as anti-viral, anti-inflammatory, anti-bacterial and anti-parasitic agents.

They may be administered parenterally or orally in admixture with a non-toxic pharmacologically acceptable inert carrier or diluent in any of the usual pharmaceutical forms. These include solid and liquid oral unit dosage forms such as tablets, capsules, powders and suspensions or solutions and suspensions for subcutaneous, intramuscular, intravenous or intra-arterial injection.

The term "unit dosage" refers to physically discrete units which may be administered in single or multiple dosages each containing a predetermined quantity of the active ingredient in association with the required diluent, carrier or vehicle. The quantity of active ingredient is the amount of the complex which is needed to produce the desired therapeutic effect.

A typical unit dosage consists essentially of from about 2.5–1000 mg. of active ingredient; however, the form in which said ingredient is administered and the frequency of administration is usually determinative of the concentration. Thus, for example, oral unit dosage forms containing 2.5–1000 mg. of active ingredient may be administered one or more times per day depending upon the severity of the tumor which is sought to be treated and the condition of the host animal. By contrast, parenteral administration generally requires from about 10–500 mg. of the active ingredient per unit dosage administered as a daily dose or as a fraction thereof depending upon whether the regimen calls for administration once, twice, three or four times daily.

By contrast to the "unit dosage", the effective dose is that dosage which is needed to achieve the desired anti-tumor cell effect. In general, this dosage lies within the range of from about 1–2000 mg. of the active ingredient per kg. of body weight of the host animal. A preferred concentration lies within the range of from about 2.5–1000 mg./kg. of body weight. For oral administration it has been found that an effective dose of 5–2000 mg./kg. is most suitable, whereas, in the case of parenteral administration it is usually advisable to employ from about 1–320 mg./kg. These dosages are well below the toxic or lethal dose and they may be varied over a wide range for adjustment to the patient which is being treated.

In this invention the term "pharmacologically acceptable inert carrier or diluent" denotes a non-toxic substance which, when mixed with the active ingredient, renders it more suitable for administration. Compositions intended for oral administration may include such carriers or diluents as glucose, lactose, sucrose, corn starch, potato starch, sodium carboxymethyl cellulose, ethyl cellulose, cellulose acetate, powdered gum tragacanth, gelatin, alginic acid, agar, stearic acid or the sodium, calcium and magnesium salts of stearic acid, sodium lauryl sulfate, polyvinylpyrrolidone, sodium citrate, calcium carbonate and dicalcium phosphate. Said compositions may also contain non-toxic adjuvants and modifiers such as dyes, buffering agents, preservatives, surfactants, emulsifiers, flavoring agents or biocides and the like.

Tablets are prepared by mixing a complex of this invention in a suitably comminuted or powdered form with a diluent or base such as starch, sucrose, kaolin, di-calcium phosphate and the like. The resulting mixture can be granulated by wetting with a binder such as a syrup, starch (paste), acacia mucilage or solutions of cellulosic or polymeric materials, whereafter, the wetted mixture is forced through a screen. As an alternative to granulating, the powdered mixture can be run through a tablet machine and imperfectly formed slugs broken into granules. The granules are lubricated to prevent sticking to the tablet-forming dies via the addition of stearic acid, a stearate salt, talc or mineral oil and the lubricated mixture is then compressed into tablets. The complexes can also be combined with free flowing inert carriers followed by compression into tablets without going through the granulating or slugging steps. A protective coating or sealing coat of shellac, sugar or polymeric material and a polished coating of wax can also be provided. Dyestuffs may be added to distinguish different unit dosages.

Capsules are formulated by preparing a powdered mixture, according to the procedure hereinbefore described and pouring said mixture into preformed gelatin sheaths. A lubricant such as talc, magnesium stearate or calcium stearate can be added as an adjuvant prior to the filling operation. A glidant such as colloidal silica may be added to improve the flow characteristics and a disintegrating or solubilizing agent may also be added to enhance the effectiveness of the medicament upon ingestion.

Powders are prepared by comminuting the compound to a fine size and mixing with a similarly comminuted pharmaceutical diluent or carrier such as an edible carbohydrate as, for example, starch. Sweetening agents and flavorings, preservatives and dispersing and/or coloring agents may also be employed.

Oral fluids such as syrups and elixirs are prepared in unit dosage form so that a given quantity of medicament, such as a teaspoonful, will contain a predetermined amount of the active ingredient. Suspensions can be formulated by dispersing the active ingredient in a non-toxic vehicle in which it is essentially insoluble.

Fluid unit dosage forms for parenteral administration can be prepared by placing a measured amount of the complex in an ampoule or vial which is sterilized and sealed. An accompanying vial or vehicle can be provided for mixing with said complex prior to administration.

This invention also provides for combining two or more of the subject complexes into a single unit dosage form or, alternatively, combining one or more of said complexes with other known anti-tumor agents, therapeutic agents or nutritive agents and the like so as to enhance or complement the anti-tumor effect.

The preferred compositions for oral administration are tablets in which the lactate complex is present in quantities of 2.5–1000 mg. but, preferably, 5–500 mg. in a pharmaceutically acceptable orally ingestible solid carrier. If desired, the composition may also contain flavors, binders, lubricants and other excipients known in the art.

A preferred alternative for oral administration is the soft gelatin capsule. Such a composition may contain from 2.5–1000 mg. but, preferably, 5–500 mg. by weight of active ingredient dissolved or suspended in vegetable oil, peanut oil, alcohol or glycerine and the like.

The following embodiments illustrate representative unit dosage forms.

COMPRESSED TABLET

A tablet suitable for swallowing is prepared by mixing the following ingredients:

| | |
|---|---|
| Cis-Dichlorobis(2-Methyl-2-Amino-1,3-Propanediol)platinum(II) | 150 mg. |
| Niacinamide | 50 mg. |
| Calcium Pantothenate | 20 mg. |
| Magnesium Sulfate | 50 mg. |
| Zinc Sulfate | 50 mg. |
| Magnesium Stearate | 10 mg. |
| | 330 mg. |

The cis-dichlorobis(2-methyl-2-amino-1,3-propanediol)platinum(II), niacinamide, calcium pantothenate, magnesium sulfate, zinc sulfate and magnesium stearate (5.0 mg.) are mixed and compressed into slugs. The slugs are then broken into granules and sifted through an 8 mesh screen. Additional magnesium stearate (5.0 mg.) is added and the mixture is then compressed into tablets suitable for oral administration.

Soft Gelatin Capsule

A soft elastic gelatin capsule is filled with the following ingredients:

| | |
|---|---|
| Cis-Dichlorobis[Tris(Hydroxymethyl)-Methylamine]platinum(II) | 100 mg. |
| Wheat germ oil | 50 mg. |
| Sunflower seed oil | 100 mg. |
| | 250 mg. |

The cis-dichlorobis[tris(hydroxymethyl)methylamine]platinum(II) and wheat germ oil are mixed with sunflower seed oil and the resulting mixture is poured into gelatin capsules suitable for oral administration. An alternative embodiment provides for substituting sunflower seed oil and wheat germ oil with equal amounts of peanut oil to obtain an otherwise similar capsule which is also suitable for oral administration.

Dry Filled Capsule

A hard dry-filled capsule may be prepared from the following ingredients:

| | |
|---|---|
| Malonato(2-Methyl-2-Amino-1,3-Propanediol)platinum(II) | 200 mg. |
| Niacinamide | 50 mg. |
| Calcium Pantothenate | 10 mg. |
| Sodium Lactate | 150 mg. |
| | 410 mg. |

The cis-dichlorobis(2-methyl-2-amino-1,3-propanediol)platinum(II) is reduced to a No. 60 powder. Niacinamide, calcium pantothenate and sodium lactate are passed through a No. 60 bolting cloth and these ingredients are added to the cis-dichlorobis(2-methyl-2-amino-1,3-propanediol)platinum(II). This combination of ingredients is mixed for 10 minutes and then poured into a No. 3 size gelatin capsule.

Dry Powder

The following composition illustrates a representative dosage in dry powder form. In this embodiment the active ingredient is water soluble and it is combined with up to 60% by weight of a suitable flavoring agent. All quantities are in a weight-percent relationship.

| | |
|---|---|
| Cis-Dichlorobis(2-Methyl-2-Amino-1,3-Propanediol)platinum(II) | 25-90% |
| Flavoring Agent | 10-60% |
| Preservative | 0-1.0% |

The cis-dichlorobis(2-methyl-2-amino-1,3-propanediol)platinum(II) flavoring agent and preservative are thoroughly blended to afford a momogeneous dry powder which is readily soluble in water. The resulting formulation may be blended with other therapeutic agents to afford combination-type medicinals. Alternatively, said powder may be dissolved in a pharmacologically acceptable diluent to afford a solution which is suitable for oral administration.

Compositions intended for parenteral administration may include such diluents and carriers as water-miscible solvents as, for example, sesame oil, groundnut oil, aqueous propylene glycol and a solution of sodium lactate. Typical of said compositions are solutions which contain the active ingredient in sterile form. An embodiment illustrating a dosage form suitable for intravenous injection is set forth below.

Parenteral Solution

Injectable solutions can be formulated by mixing an ampoule of active ingredient with an ampoule of sterile diluent:

| | | |
|---|---|---|
| Ampoule: | Cis-Dichlorobis[Tris(Hydroxymethyl)-Methylamine]platinum(II) | 200 mg. |
| Ampoule: | Sterile Saline (Diluent for Injection) | 2 cc. |

The cis-dichlorobis[tris(hydroxymethyl)methylamine]platinum(II) and water are mixed thoroughly immediately prior to administration. If desired, one or more other active ingredients may be added to provide an injectable solution having enhanced therapeutic activity.

The following embodiments illustrate the methods by which the products (I) of this invention are obtained; however, it is to be understood that said embodiments are merely illustrative and they are not to be construed as being limitative of the invention herein described and claimed.

EXAMPLE 1

Cis-Dichlorobis(2-Methyl-2-Amino-1,3-Propanediol)-Platinum(II)

Potassium tetrachloroplatinate (1.66 g, 4 mmoles) was dissolved in water (16 ml) and a solution of potassium iodide (2.72 g, 16 mmoles) in water (5 ml) was added. This mixture was stirred for 15 minutes at room temperature. A solution of 2-methyl-2-amino-1,3-propanediol (0.84 g, 8 mmoles) in water (5 ml) was added and the mixture was stirred for an additional 15 minutes.

A solution of silver nitrate (5.44 g, 32 mmoles) in water (5 ml) was added and the resulting mixture was stirred for 15 minutes. The silver chloride and silver iodide which formed were then filtered and 1M hydrochloric acid (12 ml, 12 mmoles) was added. The solution was warmed to approximately 70° C. and then stirred for 30 minutes while cooling occurred. The resulting solution was evaporaed to near dryness at 40° C. on a rotary evaporator, ethanol (25 ml) was added, whereupon, a white precipitate formed. This precipitate, identified as potassium nitrate, was removed by filtration and the filtrate was again reduced to dryness. Acetone (10 ml) was added and the product was allowed to crystallize overnight in a freezer. There was thus obtained 0.49 g (25.7%) of cis-dichlorobis(2-methyl-2-amino-1,3-propanediol)platinum(II). The solubility of this product in water is approximately 900 mg/ml.

| Analysis for $PtC_8H_{22}N_2O_4Cl_2$: | | | | |
|---|---|---|---|---|
| | % Pt | % C | % H | % N |
| Calculated: | 40.96 | 20.17 | 4.66 | 5.88 |
| Found: | 37.13 | 19.44 | 3.92 | 5.58 |

EXAMPLE 2

Cis-Dichlorobis[Tris(Hydroxymethyl)methylamine]-Platinum(II)

The procedure of Example 1 was repeated except that tris(hydroxymethyl)methylamine was substituted for the 2-methyl-2-amino-1,3-propanediol therein described. There was thus obtained a crystalline product identified as cis-dichlorobis[tris(hydroxymethyl)methylamine]platinum(II).

The procedure of Example 1 is repeated using polyhydroxylated amines other than the 2-methyl-2-amino-1,3-propanediol therein described. The following Table illustrates the starting materials and the products which result according to this procedure.

TABLE 1

Cis-[Pt(A)$_2$(X)$_2$] PRODUCTS

| Example | A (Monodentate Amine) | X |
|---|---|---|
| 3 | *HOCH$_2$—[CH(OH)]$_3$—CH(NH$_2$)—CHO | Cl |
| 4 | HOCH$_2$—C(CH$_3$)(NH$_2$)—CH$_2$OH | Br |
| 5 | HOCH$_2$—C(CH$_3$)(NH$_2$)—CH$_2$OH | Lactato |
| 6 | HOCH$_2$—C(CH$_2$OH)(CH$_2$OH)—NH$_2$ | ½ Malonato |
| 7 | HOCH$_2$—CH(OH)—CH$_2$—NH$_2$ | I |
| 8 | HOCH$_2$—C(CH$_2$OH)(CH$_2$OH)—CH$_2$—NH$_2$ | ½ SO$_4$ |
| 9 | HOCH$_2$—C(NH$_2$)(C$_2$H$_5$)—CH$_2$OH | ½ Ethylmalonato |
| 10 | HOCH$_2$—[CHOH]$_4$—CH$_2$NH$_2$ | Bromoacetato |
| 11 | (HOCH$_2$)$_3$CCH$_2$CH$_2$NH$_2$ | ½ Cyclobutane-dicarboxylato |

*Glucosamine.

The procedure of Example 1 is again repeated using polyhydroxylated diamines (A$_2$) in lieu of the 2-methyl-2-amino-1,3-propanediol therein described. The following Table illustrates the starting materials and the resultant products:

TABLE 2

Cis-[PtA$_2$(X)$_2$] PRODUCTS

| Example | A$_2$ (Bidentate Amine) | X |
|---|---|---|
| 12 | *HOCH$_2$—CHOH—CH—C(NH$_2$)=C(NH$_2$)—CO (with O bridge) | Cl |
| 13 | HO—, HO— substituted S ring with two NH$_2$ | Br |
| 14 | HOCH$_2$—CH$_2$—C(CH$_2$OH)$_2$—CH(NH$_2$)—CH$_2$NH$_2$ | ½ HPO$_4$ |
| 15 | OH, HO— substituted S ring with two NH$_2$ and OH | ½ phthalato |
| 16 | (HOCH$_2$)$_3$C—(NH$_2$)(NH$_2$) | ½ ketomalonato |
| 17 | (HOCH$_2$)(HOCH$_2$)C(NH$_2$)(NH$_2$) | propionate |

*2,3-Diamino-2,3-dideoxyascorbic acid

ANTI-TUMOR EVALUATION

The above-prepared compounds were evaluated against S180 ascites in female CFW Swiss mice. The mice were weighed (Average weight: 20 g), placed into cages (four or six mice to a cage) and on day zero the mice were inoculated with 0.2 ml of a freshly prepared saline suspension (0.15M NaCl) containing $1 \times 10^7$ tumor cells/ml or a total of $2 \times 10^6$ cells. This inoculum was freshly prepared using "transfer" mice which had been injected with tumor cells the previous week; it was obtained via the following steps: (1) the removal of cells from the peritoneal cavity of the sacrificed transfer mouse, (2) alternate configuration and washing operations (2–3 times with cold saline) to remove blood and other components, and (3) dilution of the volume of the packed cell with saline (1:3). A final centrifugation was carried out at 1000 RPM over a two minute period. A cell count was made on a 2,000-fold dilution of this 1:3 suspension by means of a Coulter Counter. A final dilution to $1 \times 10^7$ cells/ml was made based on the average count.

On day 1, solutions of the test compounds were prepared and each mouse in a set of six were injected with the same test compound at the same dosage. The doses were based on the average weight of the animals (cage weight). Also, beginning on day 1 two controls were employed containing six mice per control:

(1) Normal; Control: This consisted solely of the carrier or diluent used in combination with the test compound; and
(2) Positive Control: This consisted solely of the known anti-tumor agent cis-[Pt(NH$_3$)$_2$Cl$_2$] in saline (8 mg/kg) to test the response of the biological system.

The effectiveness of a test compound was measured in terms of the % increase in life span (%ILS) of the test mice relative to the Normal Control (Calculated from the day of tumor inoculation, i.e., day zero). To standardize the test data and permit intercomparisons, the day of evaluation was arbitrarily taken as that day corresponding to twice the mean life span (or average day of death) of the control. This established a practical upper limit of 100% on the %ILS attainable. For calculation purposes the survivors on the day of evaluation were considered to have died on that day. The %ILS was calculated as follows:

$$\% ILS = \left( \frac{\text{mean-life span of test mice}}{\text{mean-life span of control mice}} - 1 \right) \times 100\%$$

ILS values in excess of 50% were interpreted as being indicative of anti-tumor activity, whereas, values in excess of 75% indicated excellent activity.

The test compounds were evaluated in water and compared against the known anti-tumor agents. The results of this study are shown in Table 3:

TABLE 3

Cis-[Pt(II)(A)₂Cl₂] Complexes
Anti-Tumor Screening Data; S 180 Ascites

| Example [Amine Ligand] | Dose (mg/kg) | % ILS | Survivors | Positive Control % ILS | Survivors |
|---|---|---|---|---|---|
| Ex. 1 | 12.5 | 67 | 1 of 4 | 70 | 4 of 6 |
| [2-Methyl-2- | 25 | 83 | 2 of 4 | | |
| amino-1,3-pro- | 50 | 69 | 1 of 4 | | |
| panediol] | 100 | 100 | 4 of 4 | | |
| | 200 | −49 | 0 of 4 | | |
| | 400 | −71 | 0 of 4 | | |
| Ex. 2 | 10 | −8 | 0 of 4 | 77 | 2 of 6 |
| [Tris(hydroxy- | 20 | 2 | 0 of 4 | | |
| methyl)methyl- | 40 | 7 | 0 of 4 | | |
| amine] | 80 | 34 | 1 of 4 | | |
| | 160 | 62 | 1 of 4 | | |
| | 320 | 68 | 2 of 4 | | |

On the basis of the data in Table 3 it can be concluded that the platinum(II) complexes of this invention are effective anti-tumor agents.

The effective dose (ED₉₀), lethal dose (LD₅₀) and therapeutic index (TI) for these compounds were determined according to the method of Miller and Tainter (Reported by R. A. Turner, "Screening Methods in Pharmacology", Academic Press, New York, Page 61-62 (1976)).

The therapeutic index for cis-dichlorobis(2-methyl-2-amino-1,3-propanediol)platinum(II) is 7.2, a value which compares favorably with the 2.2-2.5 attributed to Cisplatin.

The products herein-described are merely illustrative of the invention and they are capable of wide variation and modification. Alterations to the product molecule are within the skill of the artisan to effect and, therefore, any derivatives of the herein-described compounds which prove useful in the treatment of tumors are considered as being within the scope of this invention.

What is claimed is:

1. A compound having the formula:

wherein
A₂ is a polyhydroxy substituted bidentate amine of the formula:

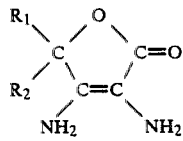

wherein R₁ and R₂ are selected from the group consisting of hydrogen, C₁₋₆ alkyl, or C₁₋₆ mono or polyhydroxyalkyl provided that R₁ and R₂ taken together contain two or more hydroxyl groups, or A is a polyhydroxy substituted monodentate amine of the formula:

R₁NH₂ wherein R₁ is a carbohydrate moiety derived from glucose, fructose, galactose, sucrose, or lactose, and X is an anionic ligand selected from the group consisting of halide and carboxylate, or X₂ is selected from the group consisting of dicarboxylate anion, sulfate, orthophosphate, pyrophosphate, and a combination of aquo and sulfate, orthophosphate, or pyrophosphate.

* * * * *